(12) United States Patent
Jang et al.

(10) Patent No.: US 12,090,166 B2
(45) Date of Patent: Sep. 17, 2024

(54) PHARMACEUTICAL COMPOSITION FOR PREVENTING OR TREATING DENTIN-DENTAL PULP DISEASE OR PERIODONTAL DISEASE, CONTAINING LPAR2 INHIBITOR

(71) Applicant: PUSAN NATIONAL UNIVERSITY INDUSTRY-UNIVERSITY COOPERATION FOUNDATION, Busan (KR)

(72) Inventors: Il Ho Jang, Yangsan-si (KR); Eun Jin Seo, Yangsan-si (KR); Jae Young Kim, Daegu (KR); Hyung Joon Kim, Yangsan-si (KR); Gabor J. Tigyi, Memphis, TN (US); Jung Hong Ha, Daegu (KR); Da Sol Kim, Yangsan-si (KR)

(73) Assignee: Stemden USA, LLC, Memphis, TN (US)

( * ) Notice: Subject to any disclaimer, the term of this patent is extended or adjusted under 35 U.S.C. 154(b) by 901 days.

(21) Appl. No.: 17/059,198

(22) PCT Filed: Aug. 9, 2019

(86) PCT No.: PCT/KR2019/010018
§ 371 (c)(1),
(2) Date: Nov. 25, 2020

(87) PCT Pub. No.: WO2020/032651
PCT Pub. Date: Feb. 13, 2020

(65) Prior Publication Data
US 2021/0196743 A1  Jul. 1, 2021

(30) Foreign Application Priority Data
Aug. 9, 2018 (KR) .......... 10-2018-0092912
Aug. 7, 2019 (KR) .......... 10-2019-0096229

(51) Int. Cl.
*C07H 21/04* (2006.01)
*A23L 33/13* (2016.01)
*A61K 31/713* (2006.01)
*A61P 1/02* (2006.01)

(52) U.S. Cl.
CPC .......... *A61K 31/713* (2013.01); *A23L 33/13* (2016.08); *A61P 1/02* (2018.01)

(58) Field of Classification Search
None
See application file for complete search history.

(56) References Cited

U.S. PATENT DOCUMENTS

| 2016/0032247 A1 | 2/2016 | Kato et al. |
| 2017/0042915 A1 | 2/2017 | Tremblay et al. |
| 2020/0215085 A1* | 7/2020 | Wilson ............... A61K 9/0073 |

FOREIGN PATENT DOCUMENTS

| JP | 2014-088333 A | 5/2014 |
| KR | 10-2009-0033643 A | 4/2009 |
| KR | 10-2012-0089547 A | 8/2012 |
| KR | 10-2014-0095295 A | 8/2014 |
| WO | 2012-109569 A1 | 8/2012 |

OTHER PUBLICATIONS

Geraldo et al. Signal Transduction and Targeted Therapy (2021) 6:45).*
Hongying Pan et al., "Lysophosphatidic Acid Rescues Human Dental Pulp Cells from Ischemia-induced Apoptosis",—Journal of Endodontics, vol. 40, No. 2, Feb. 2014, pp. 217-222.
International Search Report for PCT/KR2019/010018 mailed Nov. 25, 2019 from Korean Intellectual Property Office.
Seo, E. J. et al., "Inhibition of Lysophosphatidic Acid Receptor 2 Expedites Odontoblastic Differentiation of Dental Pulp Stem Cells", In: 2018 IUBMB Seoul, 24th IUBMB Congress and 15th FAOBMB Congress. Jun. 4-8, 2018, p. 05-020.
Kim, D. S. et al., "Inhibition of Lysophosphatidic Acid Receptor 2 Expedites Odontoblastic Differentiation of Dental Pulp Stem Cells", KSSCR 2017, Annual meeting, Aug. 17-18, 2017, p. 008.
Kim, D. S. et al., "Inhibition of Lysophosphatidic Acid Receptor 2 Expedites Odontoblastic Differentiation of Human Dental Pulp Stem Cells", ISSCR 2018, Annual meeting, Jun. 20-23, 2018, T-2115.
Jeong, K. J. et al., "Lysophosphatidic acid receptor 2 and Gi/Src pathway mediate cell motility through cyclooxygenase 2 expression in CAOV-3 ovarian cancer cells", Experimental & molecular medicine, Dec. 2018, vol. 40, No. 6, pp. 607-616.

* cited by examiner

*Primary Examiner* — Kimberly Chong
(74) *Attorney, Agent, or Firm* — Veeitary GroupIP PLLC; Susan Fentress

(57) ABSTRACT

The present invention relates to a pharmaceutical composition for preventing or treating dentin-dental pulp disease or periodontal disease, a quasi-drug composition for preventing or improving dentin-dental pulp disease or periodontal disease or a health functional food composition for preventing or improving dentin-dental pulp disease or periodontal disease, all of which comprise a LPAR2 (lysophosphatidic acid receptor 2) inhibitor.

4 Claims, 10 Drawing Sheets
Specification includes a Sequence Listing.

(A)

(B)

SEQUENCE LISTING

```
<160> NUMBER OF SEQ ID NOS: 13

<210> SEQ ID NO 1
<211> LENGTH: 42
<212> TYPE: RNA
<213> ORGANISM: Artificial Sequence
<220> FEATURE:
<223> OTHER INFORMATION: LPAR2 (siRNA)
<220> FEATURE:
<221> NAME/KEY: misc_feature
<222> LOCATION: (20)..(21)
<223> OTHER INFORMATION: n=t
<220> FEATURE:
```

<221> NAME/KEY: misc_feature
<222> LOCATION: (41)..(42)
<223> OTHER INFORMATION: n=t

<400> SEQUENCE: 1
ggccaacuca cuggucaaun nauugaccag ugaguuggcc nn                42

<210> SEQ ID NO 2
<211> LENGTH: 18
<212> TYPE: DNA
<213> ORGANISM: Artificial Sequence
<220> FEATURE:
<223> OTHER INFORMATION: Primer (GAPDH - Forward)

<400> SEQUENCE: 2
gaaggtgaag gtcggagt                                           18

<210> SEQ ID NO 3
<211> LENGTH: 20
<212> TYPE: DNA
<213> ORGANISM: Artificial Sequence
<220> FEATURE:
<223> OTHER INFORMATION: Primer (GAPDH - Reverse)

<400> SEQUENCE: 3
gaagatggtg atgggatttc                                         20

<210> SEQ ID NO 4
<211> LENGTH: 21
<212> TYPE: DNA
<213> ORGANISM: Artificial Sequence
<220> FEATURE:
<223> OTHER INFORMATION: Primer (OPN - Forward)

<400> SEQUENCE: 4
ctccattgac tcgaacgact c                                       21

<210> SEQ ID NO 5
<211> LENGTH: 23
<212> TYPE: DNA
<213> ORGANISM: Artificial Sequence
<220> FEATURE:
<223> OTHER INFORMATION: Primer (OPN - Reverse)

<400> SEQUENCE: 5
caggtctgcg aaacttctta gat                                     23

<210> SEQ ID NO 6
<211> LENGTH: 23
<212> TYPE: DNA
<213> ORGANISM: Artificial Sequence
<220> FEATURE:
<223> OTHER INFORMATION: Primer (RUNX2 - Forward)

<400> SEQUENCE: 6
tcttagaaca aattctgccc ttt                                     23

<210> SEQ ID NO 7
<211> LENGTH: 21
<212> TYPE: DNA
<213> ORGANISM: Artificial Sequence
<220> FEATURE:
<223> OTHER INFORMATION: Primer (RUNX2 - Reverse)

```
<400> SEQUENCE: 7
tgctttggtc ttgaaatcac a                                        21

<210> SEQ ID NO 8
<211> LENGTH: 20
<212> TYPE: DNA
<213> ORGANISM: Artificial Sequence
<220> FEATURE:
<223> OTHER INFORMATION: Primer (DMP-1 - Foward)

<400> SEQUENCE: 8
caagacagtg cccaagatac                                          20

<210> SEQ ID NO 9
<211> LENGTH: 18
<212> TYPE: DNA
<213> ORGANISM: Artificial Sequence
<220> FEATURE:
<223> OTHER INFORMATION: Primer (DMP-1 - Reverse)

<400> SEQUENCE: 9
ttccctcatc gtccaact                                            18

<210> SEQ ID NO 10
<211> LENGTH: 20
<212> TYPE: DNA
<213> ORGANISM: Artificial Sequence
<220> FEATURE:
<223> OTHER INFORMATION: Primer (DSPP - Forward)

<400> SEQUENCE: 10
ctggtgcatg aaggtgatag                                          20

<210> SEQ ID NO 11
<211> LENGTH: 20
<212> TYPE: DNA
<213> ORGANISM: Artificial Sequence
<220> FEATURE:
<223> OTHER INFORMATION: Primer (DSPP - Reverse)

<400> SEQUENCE: 11
ccctcttcgt ttgctaatgt                                          20

<210> SEQ ID NO 12
<211> LENGTH: 23
<212> TYPE: DNA
<213> ORGANISM: Artificial Sequence
<220> FEATURE:
<223> OTHER INFORMATION: Primer (LPAR2 - Forward)

<400> SEQUENCE: 12
gtcctcatta cccagtcata ccg                                      23

<210> SEQ ID NO 13
<211> LENGTH: 23
<212> TYPE: DNA
<213> ORGANISM: Artificial Sequence
<220> FEATURE:
<223> OTHER INFORMATION: Primer (LPAR2 - Reverse)

<400> SEQUENCE: 13
ctgatggact ccacccttta gct                                      23
```

PHARMACEUTICAL COMPOSITION FOR PREVENTING OR TREATING DENTIN-DENTAL PULP DISEASE OR PERIODONTAL DISEASE, CONTAINING LPAR2 INHIBITOR

CROSS REFERENCE TO PRIOR APPLICATIONS

This application is the 35 U.S.C. 371 national stage of International application PCT/KR2019/010018 filed on Aug. 8, 2019; which claims priority to Korean application 10-2019-0096229 filed on Aug. 7, 2019, and Korean application 10-2018-0092912 filed on Aug. 9, 2018. The entire contents of each of the above-identified applications are hereby incorporated by reference.

ACKNOWLEDGEMENTS

The invention was supported by the National Research Foundation of Korea(NRF) grant funded by the Korea government (NRF-2018R1D1A1A02048916) and 2020 Public Technology Based Market Related Startup Search Support Business' of Ministry of Science and ICT.

TECHNICAL FIELD

The present invention relates to a pharmaceutical composition for preventing or treating dentin-dental pulp disease or periodontal disease, a quasi-drug composition for preventing or improving dentin-dental pulp disease or periodontal disease or a health functional food composition for preventing or improving dentin-dental pulp disease or periodontal disease, which comprises a LPAR2 (lysophosphatidic acid receptor 2) inhibitor.

BACKGROUND ART

Dental pulp is a soft connective tissue that fills the pulp chamber inside the tooth, where nerves and blood vessels are abundantly distributed and reaches the surface layer of the dentin. A lesion that occurs on the dental pulp is called dental pulp disease.

The causes of dental pulp disease are very diverse, but in most cases, it is caused by bacterial infection by dental caries and infection into the dental pulp through perforation, fracture, crack of the tooth and periodontal pocket. It can be also caused by trauma, abrasion, tooth cracking, heat and friction from dental instruments during treatment. Pulpitis caused by bacterial infection can spread to periapical disease and periodontal disease. When dental pulp disease occurs, hyperemia of pulp, pulpitis, and pulp necrosis proceed in this order. In the case of pulp necrosis, the entire periodontal tissue disappears because the pulp dies and no blood is supplied to the pulp, and later periapical disease or abnormality of the entire tooth may be caused.

For the treatment of dental pulp and periapical diseases, a pulp replication agent and pulp canal filler are used and in general, calcium hydroxide, MTA (Mineral Trioxide Aggregate), Gutta-percha, and the like have been used. In the case of MTA, its sealing force and biocompatibility is effective in treatment, but a high cost problem arises as a dental treatment, and its discoloration results in aesthetic problems. In the case of Gutta-percha, it is an economical treatment method having good fluidity, but it is not physiological due to the loss of pulp vitality. Until now, conservative treatment methods for treating dentin or dental pulp disease have weakened or fragile teeth treated and have a risk of reinfection.

Periodontal disease refers to an inflammatory disease that occurs in the gums, periodontal ligaments, or alveolar bones, which are tissues around the teeth that support teeth. Gingivitis and periodontal disease are known to cause discomfort that significantly lowers the quality of life and cause plaque deposits by making it difficult to maintain proper cleanliness of the oral cavity, thereby causing dental caries and periodontal disease. In addition, when there is hypersensitivity, plaque control is not performed, and as a result, periodontal disease progresses and gingival regression increases, causing a vicious cycle in which hypersensitivity becomes more severe. Therefore, the ultimate result of treating periodontal disease is to restore damaged connective tissue, cementum and alveolar bone and thus for this purpose, in addition to regeneration of the periodontal ligament that supports the alveolar bone, it is necessary to regenerate the alveolar bone and cementum that the periodontal ligament can attach.

Accordingly, research for developing a therapeutic agent capable of effectively treating the dentin-dental pulp disease or periodontal disease is being actively conducted. For example, Korean Patent Publication No. 2012-0089547 discloses a composition for hard tissue formation and regeneration of dentin or dental pulp tissue comprising ameloblastic cells, epical bud cells, or a culture solution thereof as an active ingredient, and Korean Patent Publication No. 2009-0033643 discloses a novel dental sac-derived dental stem cell and a method of culturing the same.

On the other hand, lysophosphatidic acid (LPA) is a phospholipid of a lysosome in the form of a hydroxyl group by being released the second acyl group of phosphatidic acid. It is highly water-soluble, and since it was the first intermediate in the de novo synthesis of phospholipids from glycerol-3-phosphate and it rapidly changes to phosphatidic acid, so only a very small amount exists in the living body. It is produced in response to stimulation from platelets, etc., and has an enhancing and agonizing effect on fibroblasts. Recently, it is attracting attention as a bioactive lipid. In particular, many studies have been conducted on the relationship between lysophosphatidic acid (LPA) and dental pulp stem cells. Many studies have shown a relationship between LPA and mesenchymal stem cell proliferation and differentiation. However, the relationship between LPAR (LPA receptor), a receptor for lysophosphatidic acid, and periodontal stem cells has not yet been reported.

In order to develop a formulation that can more effectively treat dentin-dental pulp disease or periodontal disease causing alveolar bone and cementum dissipation, the present inventors confirmed Beck 35, an inhibitor of LPAR2, promotes the differentiation of human-derived dental pulp stem cells to odontoblasts, bones and cementoblasts and completed the present invention.

DISCLOSURE

Technical Problem

The present invention is derived from the above requirements, and an object of the present invention is to provide a pharmaceutical composition for preventing or treating dentin-dental pulp disease or periodontal disease comprising a LPAR2 inhibitor.

Another object of the present invention is to provide a method of preventing or treating dentin-dental pulp disease or periodontal disease comprising administering the pharmaceutical composition to a subject other than humans.

Another object of the present invention is to provide a composition for promoting regeneration of hard tissues including dentin, bone and cementum or dental pulp tissues comprising an LPAR2 inhibitor.

Another object of the present invention is to provide a method of promoting regeneration of hard tissues including dentin, bone and cementum or dental pulp tissues, comprising administering the composition for promoting regeneration of hard tissues or dental pulp tissues to a subject other than humans.

Another object of the present invention is to provide a composition for promoting differentiation from human-derived dental pulp stem cells into odontoblasts, osteoblasts or cementoblasts comprising a LPAR2 inhibitor Another object of the present invention is to provide a quasi-drug composition for preventing or improving dentin-dental pulp disease or periodontal disease comprising a LPAR2 inhibitor.

Another object of the present invention is to provide a health functional food composition for preventing or improving dentin-dental pulp disease or periodontal disease comprising a LPAR2 inhibitor.

The object of the present invention is not limited to those mentioned above, and other objects that are not mentioned will be clearly understood by those of ordinary skill in the art from the following description.

Technical Solution

As an embodiment for achieving the above object, the present invention provides a pharmaceutical composition for preventing or treating dentin-dental pulp disease or periodontal disease comprising a LPAR2 inhibitor.

According to one embodiment, the pharmaceutical composition may promote regeneration of hard tissues including dentin, bone and cementum or dental pulp tissues.

According to one embodiment, the pharmaceutical composition may promote the differentiation of dental pulp stem cells into odontoblasts, osteoblasts or cementoblasts.

According to one embodiment, the LPAR2 (lysophosphatidic acid receptor 2) inhibitor may be siRNA, an antibody or an antagonist.

According to an embodiment, the pharmaceutical composition may further comprise a pharmaceutically acceptable carrier, excipient or diluent.

According to an embodiment, the dentin-dental pulp disease is dentin hypersensitivity, hyperemia of pulp, pulpitis, pulp degeneration, pulp necrosis or gangrene.

According to an embodiment, the periodontal disease may be gingivitis, periodontitis, periodontal pocket or periodontal abscess.

In another aspect, the present invention provides a method of preventing or treating dentin-dental pulp disease or periodontal disease, comprising administering the composition to a subject other than humans.

In another aspect, the present invention provides a composition for promoting regeneration of hard tissues including dentin, bone and cementum or dental pulp tissues comprising a LPAR2 inhibitor.

In another aspect, the present invention provides a method of promoting regeneration of hard tissues including dentin, bone and cementum or dental pulp tissues, comprising administering the composition to a subject other than humans.

In yet another aspect, the present invention provides a composition for promoting differentiation of odontoblasts, osteoblasts or cementoblasts comprising a LPAR2 inhibitor.

In yet another aspect, the present invention provides a method for promoting differentiation of odontoblasts, osteoblasts or cementoblasts, comprising administering the composition to a subject other than humans.

In yet another aspect, the present invention provides a quasi-drug composition for preventing or improving dentin-dental pulp disease or periodontal disease comprising a LPAR2 inhibitor.

In yet another aspect, the present invention provides a health functional food composition for preventing or improving dentin-dental pulp disease or periodontal disease, comprising a LPAR2 inhibitor.

According to an embodiment, the dental disease may include at least one selected from the group consisting of dentin hypersensitivity, hyperemia of pulp, pulpitis, pulp degeneration, pulp necrosis, gangrene, gingivitis, periodontitis, periodontal pocket and periodontal abscess.

Advantageous Effects

When the inhibitor of LPAR2 of the present invention, more specifically, Beck 35, which is an inhibitor of LPAR2, is treated to periodontal stem cells, there is an effect of increasing bone differentiation of periodontal stem cells. In addition, Beck 35, an inhibitor of LPAR2, increased dentin sialophosphoprotein (DSPP) which is a differentiation gene to odontoblasts, DMP-1 (dentin matrix protein 1) which is a differentiation gene into osteoblasts or cementoblasts, and Runx2 (runt-related transcription factor 2) and osteopontin which are differentiation genes into cementoblasts, from periodontal stem cells. After drilling the enamel and dentin of the mouse's molars with a drill, exposing the pulp cavity and then treating the LPAR2 inhibitor Beck 35, the vasculature increased in the first week, and in both HE staining and MTC staining, new collagen fibers seen as pulp cavity internal tissue were confirmed in blue, and within 6 weeks, there was an effect of regenerating the dentin bridge.

83) and an antagonist of LPAR2 (H2L5186303) during the differentiation of human-derived dental pulp stem cells into bone and odontoblasts.

Figure 6:
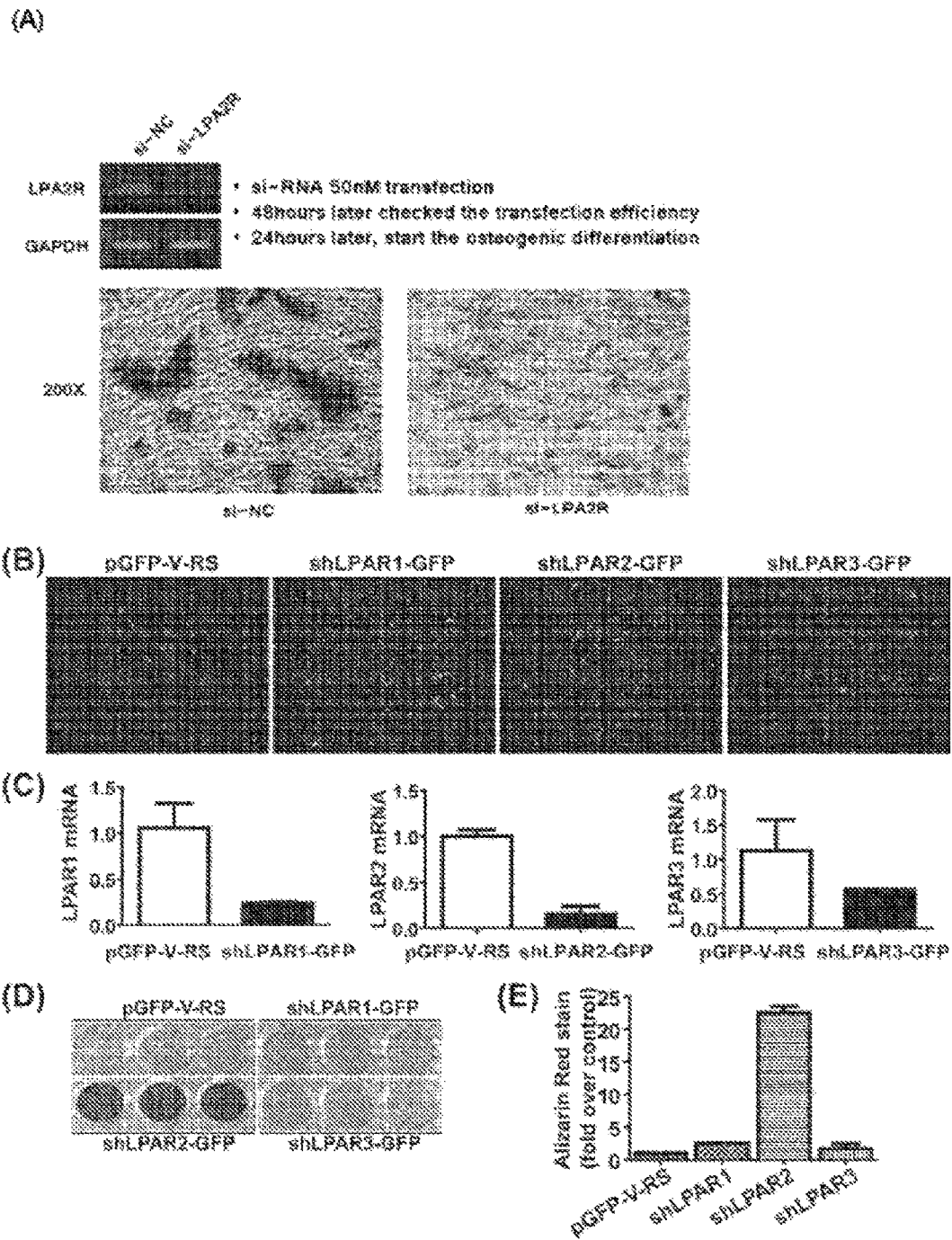

FIG. 6 is a result of confirming the degree of improvement in bone cell differentiation through Alizarin Red staining after transfecting human-derived dental pulp stem cells with si-LPAR2, and then inducing differentiation into bone and odontoblasts.

Figure 7:
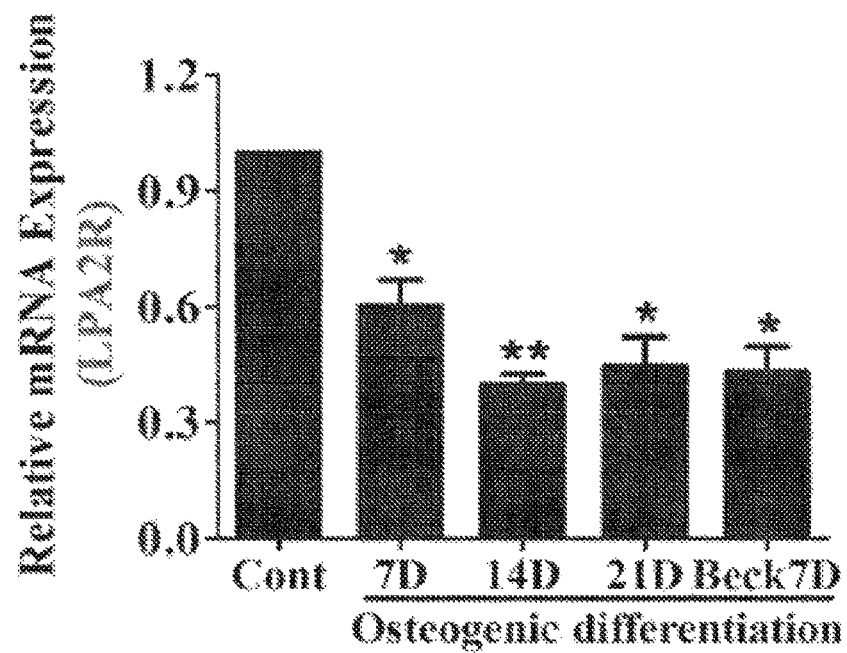

FIG. 7 shows a result of confirming the expression level of LPAR2 during differentiation from human-derived dental pulp stem cells into bone and odontoblasts.

Figure 8:
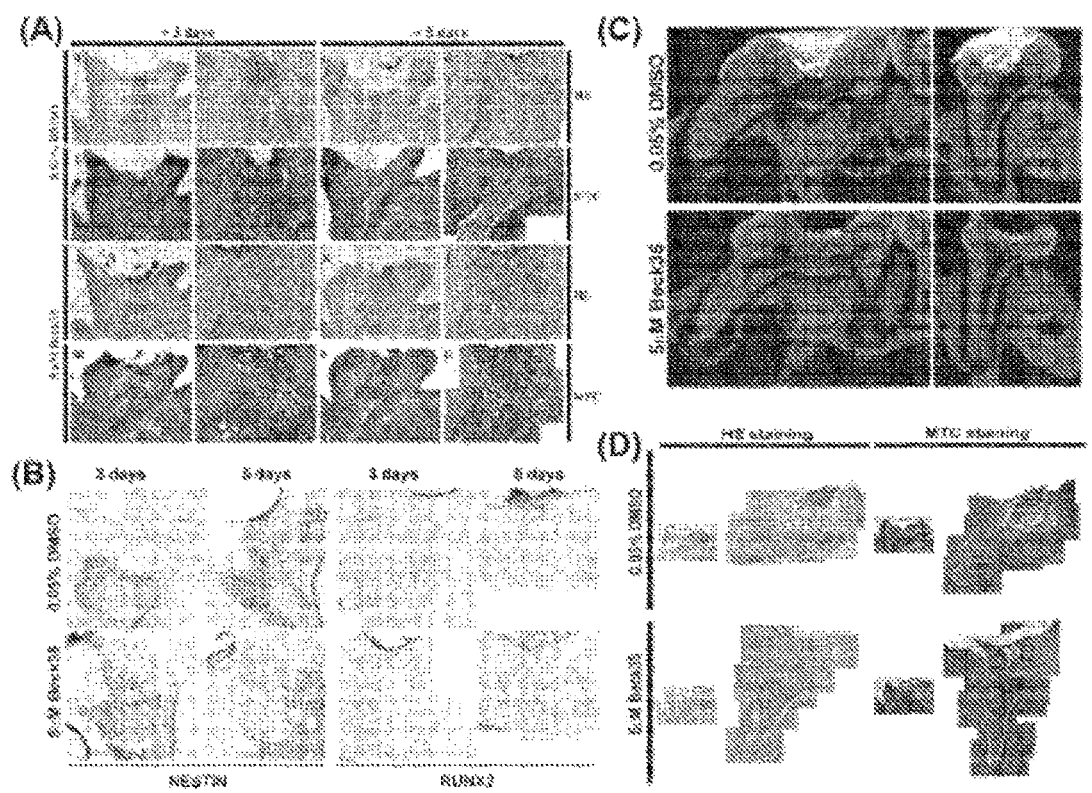

FIG. 8 shows a result of confirming the differential staining pattern of the constituents of the enamel matrix between the control group and the experimental group treated with Beck 35 in the animal model; (a) a result of confirming the enamel matrix by H&E and MTC staining; (b) the degree of expression of nestin using immunohistochemistry; and (c) the degree of hard tissue formation by micro-CT and (d) the pulp cavity.

Figure 9:
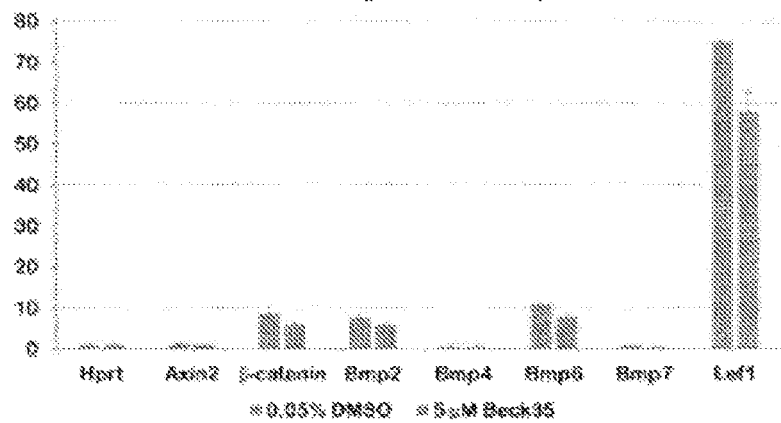
Figure 9:
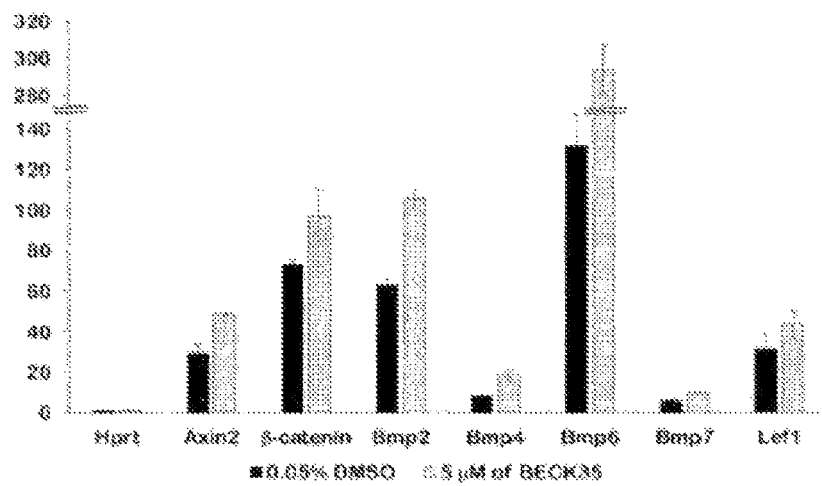

FIG. 9 shows a result of analyzing the expression levels of BMP and Wnt through RT-qPCR after in vitro culture of Beck 35 at a concentration of 5 µM in the tooth mesenchyme.

Figure 10:
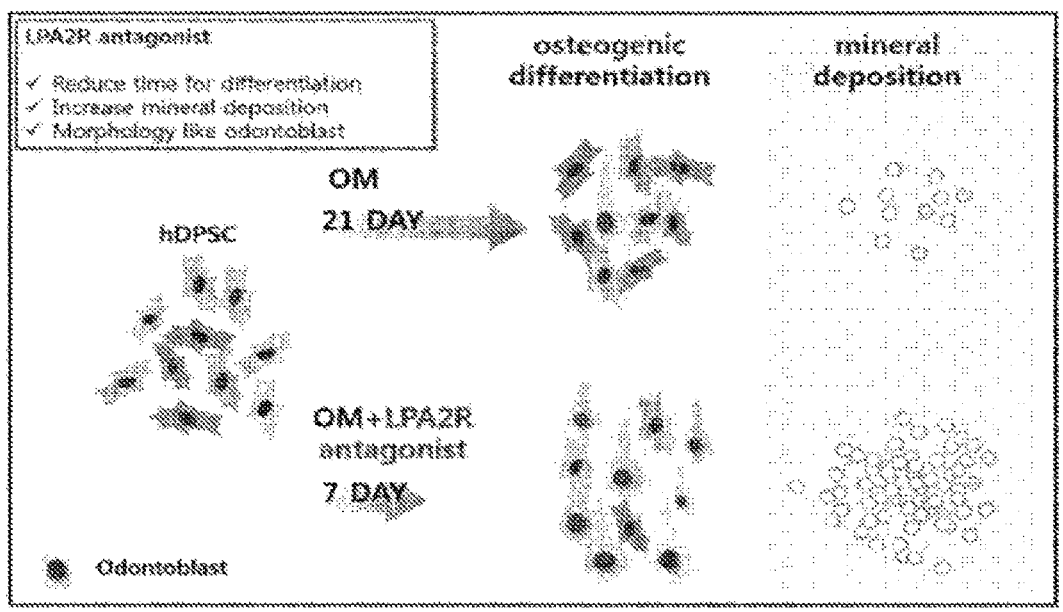

FIG. 10 shows a schematic diagram of the role of Beck 35 of the present invention in human-derived dental pulp stem cells.

BEST MODE

Hereinafter, the present invention will be described in detail.

As described above, until recently, the relationship between the LPA receptor, LPAR, and human-derived dental pulp stem cells, has not been found. Under this background, the present inventors have studied the effect of Beck 35 on the proliferation and differentiation of human-derived dental pulp stem cells by treating Beck 35, an inhibitor of LPAR2, during human-derived dental pulp stem cells differentiate into bone and odontoblasts. Thus they confirmed that Beck 35, an inhibitor of LPAR2, promotes the differentiation of human dental pulp stem cells into bone, odontoblasts and cementoblasts and further the effect of promoting the vascular growth at the beginning and regenerating the dentin bridge within 6 weeks after drilling the enamel and dentin of the mouse molars in an animal model followed by exposing the pulp cavity and treating Beck 35 and completed the present invention.

Figure 1:
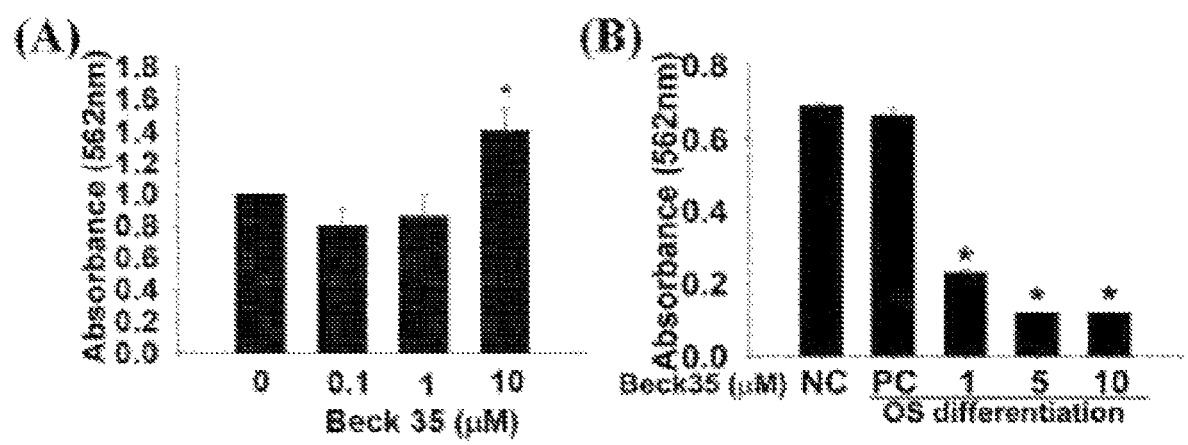
FIG. 1 is a graph showing (a) proliferation and (b) differentiation into bone cells of human-derived dental pulp stem cells according to Beck 35, an inhibitor of LPAR2.
Figure 2:
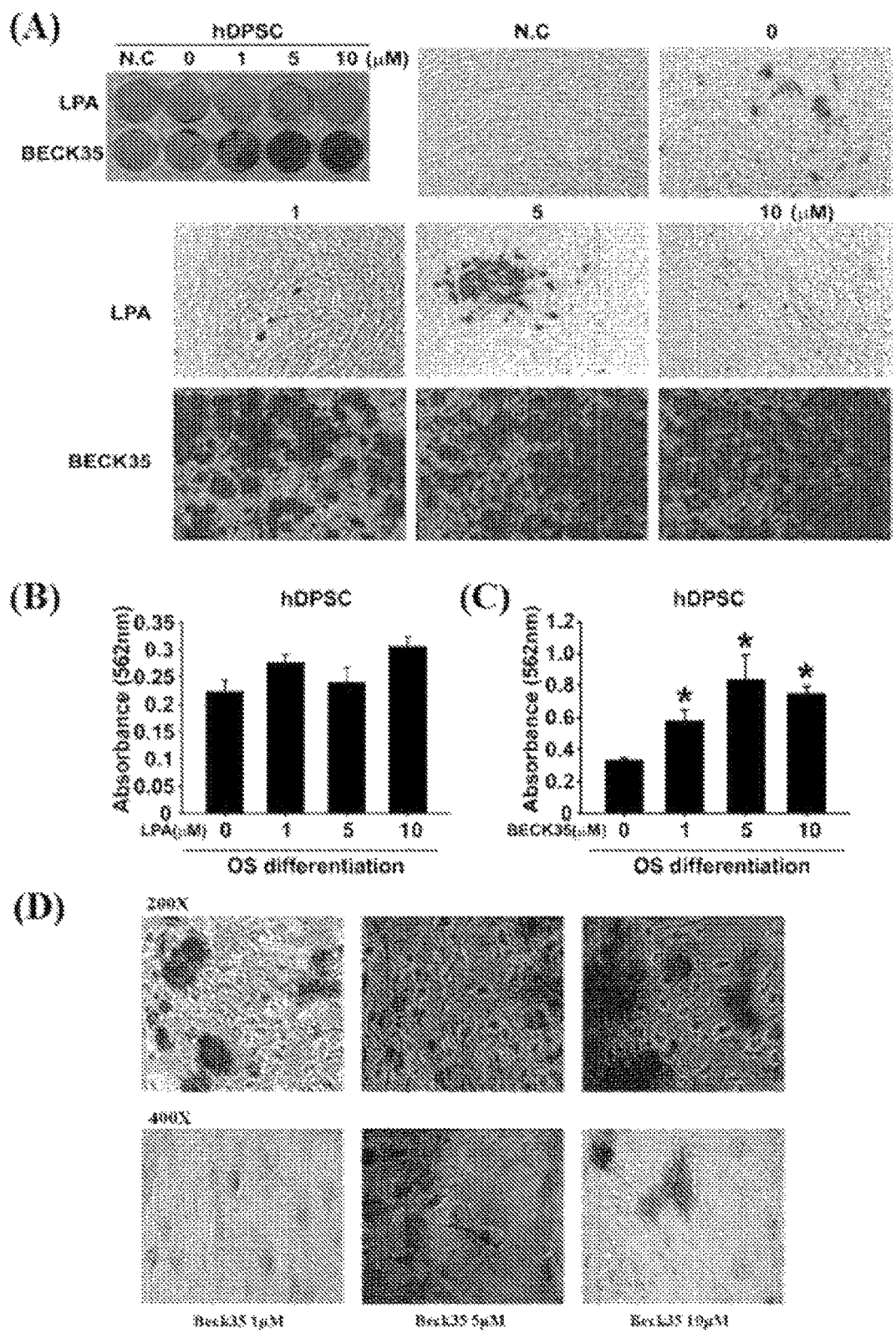
FIG. 2 shows a result of confirming the degree of improvement in bone cell differentiation through Alizarin Red staining by treatment with Beck 35, an inhibitor of LPA and LPAR2 during the differentiation of human-derived dental pulp stem cells into bone and odontoblasts.
Figure 3:
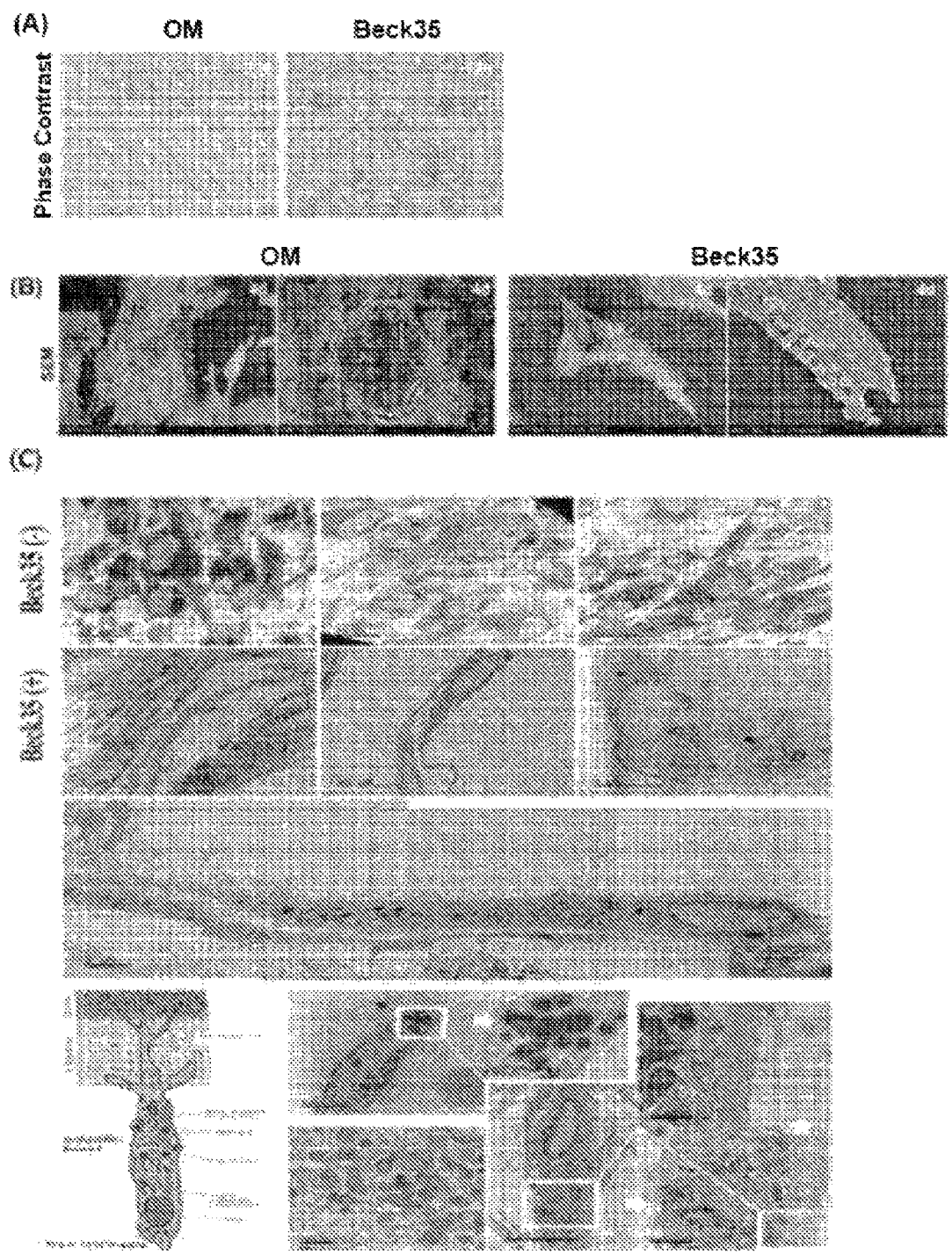
FIG. 3 shows a result of confirming the morphology of human odontoblasts through an electron microscope after treatment with Beck 35, an inhibitor of LPAR2 during the differentiation of human-derived dental pulp stem cells into bone and odontoblasts.
Figure 4:
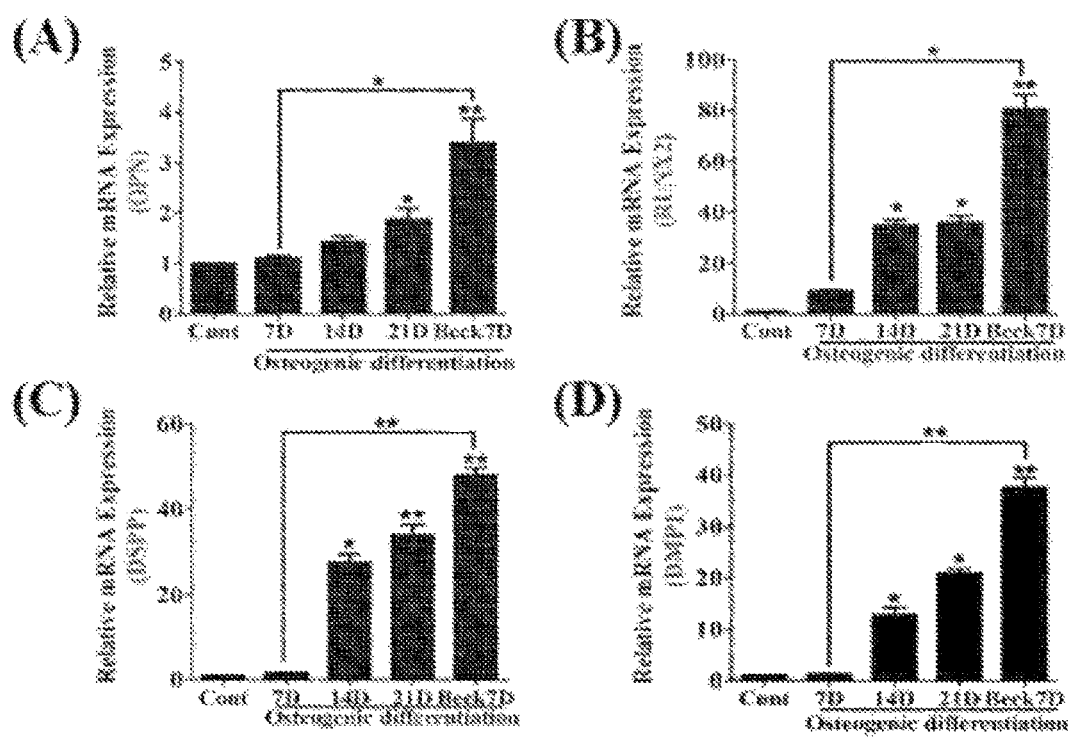
FIG. 4 shows results of confirming the expression levels of DSPP (dentin sialophosphoprotein), DMP-1 (dentin matrix protein 1), Runx2 (runt-related transcription factor 2) and osteopontin which are genes related to the differentiation of osteoblasts, odontoblasts and cementoblasts, after treating with Beck 35, an inhibitor of LPAR2 during the differentiation of human-derived dental pulp stem cells into bone and odontoblasts.

Accordingly, the present inventors sought to solve the above-described problem by providing a pharmaceutical composition for preventing or treating dentin-dental pulp disease or periodontal disease comprising an inhibitor of LPAR2. It was confirmed that Beck 35, an inhibitor of LPAR2 of the present invention, increases the proliferation of human-derived dental pulp stem cells, but reduces the proliferation of human-derived dental pulp stem cells during bone differentiation culture (FIG. 1), and has the effect of promoting the differentiation of human-derived dental pulp stem cells into bone and odontoblasts (FIG. 2 and FIG. 3). In addition, Beck 35, an inhibitor of LPAR2, promotes the differentiation of human-derived periodontal stem cells into odontoblasts, osteoblasts, or cementoblasts by increasing the expression levels of DSPP (dentin sialophosphoprotein), DMP-1 (dentin matrix protein 1), Runx2 (runt-related transcription factor 2) and osteopontin which are genes related to the differentiation of osteoblasts, odontoblasts and cementoblasts, during the differentiation of human-derived dental pulp stem cells into bone, odontoblasts and cementoblasts (FIG. 4).

Figure 5:
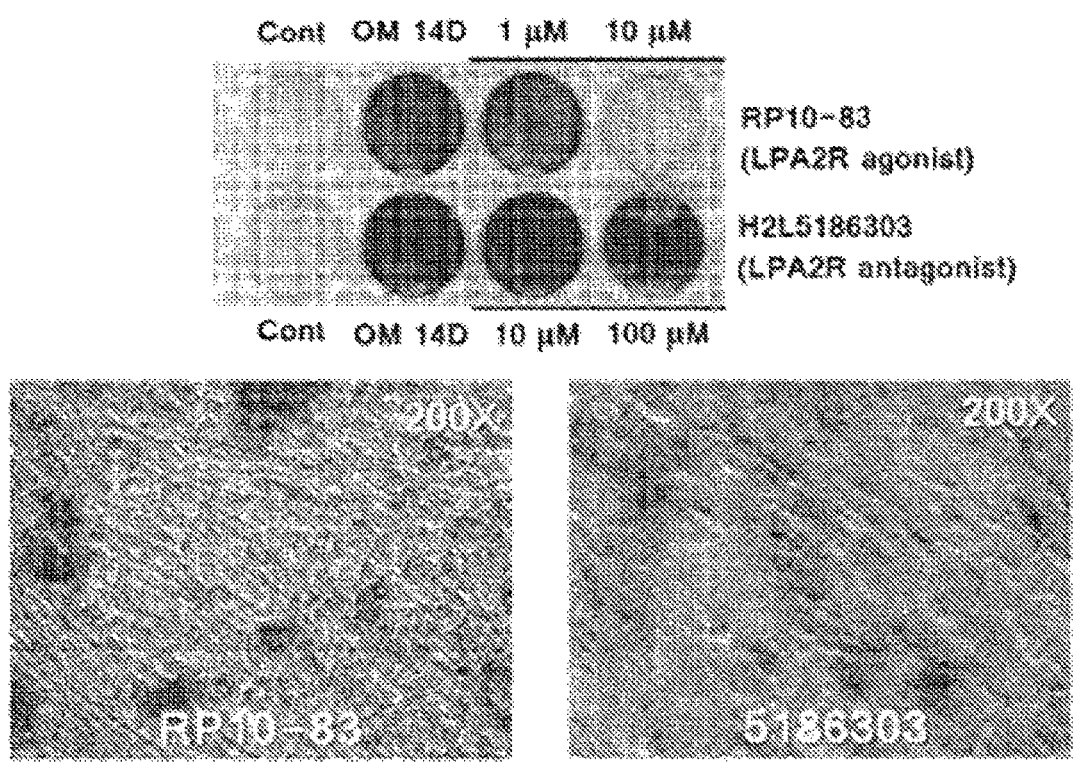
FIG. 5 shows a result of confirming the degree of improvement in bone cell differentiation through Alizarin Red staining by treatment with an agonist of LPAR2 (RP10-

As a result of treatment with an agonist of LPAR2 (RP10-83) and an antagonist of LPAR2 (H2L5186303) while human-derived dental pulp stem cells are differentiated into bone and odontoblasts, the agonist of LPAR2 (RP10-83) reduces the differentiation of bone and odontoblasts, but the antagonist of LPAR2 (H2L5186303) increased the differentiation of bone and odontoblasts like Beck 35, an inhibitor of LPAR2 (FIG. 5). Another LPAR2 inhibitor, si-LPAR2, was transfected into human-derived stem cells and then differentiated into bone and odontoblasts and observed through a microscope, and it was confirmed that the cell shape changed like Beck 35, an inhibitor of LPAR2 (FIG. 6). While human-derived dental pulp stem cells were differentiated into bone and odontoblasts, the expression of LPAR2 was confirmed to be decreased (FIG. 7).

As a result of treatment with Beck 35 in the animal model, in the group treated with Beck 35, the enamel matrix was dyed dark red, while the control group had the enamel matrix dispersed and pale dyed. Using immunohistochemistry, it was confirmed that the expression of nestin was increased in the molar dental pulp of 8-week-old B6 mice, and the enamel and dentin were drilled in the maxillary molar of 8-week-old B6 mice, and then the pulp cavity was exposed and Beck 35 5 µM was treated in the exposed pulp cavity to check whether dentin was regenerated morphologically. As a result, after Beck 35 5 µM treatment, a perfectly formed dentin bridge in the part marked with a black dotted line could be confirmed (in control group, the dentin particles was scattered). As a result of micro-CT examination, it was confirmed that the perfect dentin bridge was regenerated (FIG. 8). It was confirmed that the expression of Wnt and Bmp was also decreased after treatment with Beck 35 (FIG. 9). As described above, it was confirmed that Beck 35, an inhibitor of LPAR2, promotes the differentiation from human-derived dental pulp stem cells into bone, odontoblast and cementoblasts.

The inhibitor of LPAR2 may be a small interfering RNA (siRNA), microRNA (miRNA), an antisense oligonucleotide and an antagonist, preferably siRNA or Beck 35, more preferably Beck 35.

The Beck 35 may be the following Chemical Formula 1.

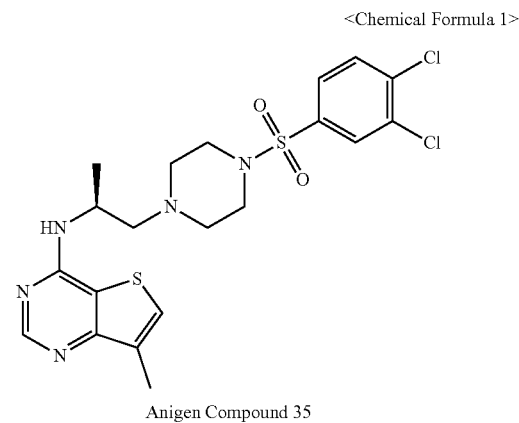 [SMILES: Cc1csc2c(N[C@@H](C)CN3CCN(S(=O)(=O)c4ccc(Cl)c(Cl)c4)CC3)ncnc12]

<Chemical Formula 1>

Anigen Compound 35

The term "dentin-dental pulp disease" of the present invention refers to a disease caused by damage to the dental pulp tissue and the dentin associated therewith due to the damage to the dental pulp tissue.

In the present invention, the dentin-dental pulp disease is not particularly limited as long as it exhibits a therapeutic effect by the pharmaceutical composition of the present invention, but as an example, dentin hypersensitivity, hyperemia of pulp, pulpitis, pulp degeneration, pulp necrosis, gangrene and the like.

The term "periodontal disease" of the present invention, also referred to as "pungchi", refers to a disease in which bacteria are infected in the gap between the gingival (gum) and teeth to damage the periodontal ligament and adjacent tissues and depending on the severity of the disease, it is divided into gingivitis and periodontitis. It is known that during the onset of the periodontal disease, inflammation progresses and more tissues are damaged, forming a periodontal pocket, and the more severe the periodontitis, the deeper the periodontal pocket becomes, and as the periodontal pocket becomes deeper, the periodontal ligament becomes inflamed and eventually bone loss is caused.

In the present invention, the periodontal disease is not particularly limited as long as it exhibits a therapeutic effect by the pharmaceutical composition of the present invention, but as an example, gingivitis, periodontitis, periodontal pocket, or periodontal abscess, etc.

The term "prevention" of the present invention refers to any action that inhibits or delays the occurrence of dentin-dental pulp disease or periodontal disease by administration of the pharmaceutical composition of the present invention.

The term "treatment" of the present invention refers to any action that treats dental pulp disease by promoting the regeneration of dentin or dental pulp tissue, or any action that treats periodontal disease by promoting the regeneration of bone and cementum, by administering the pharmaceutical composition of the present invention to a subject in need of treatment of dentin-dental pulp disease or periodontal disease.

The pharmaceutical composition of the present invention can be prepared in the form of a pharmaceutical composition for treating dentin-dental pulp disease and/or periodontal disease by further comprising a suitable carrier (natural or unnatural carrier), an excipient or a diluent commonly used in the manufacture of a pharmaceutical composition. Specifically, the each pharmaceutical composition can be formulated and used in the form of a sterile injectable solution that can be administered to the site of dentin-dental pulp disease or periodontal disease according to the usual method. In the present invention, the carriers, excipients and diluents that may be included in the pharmaceutical composition include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, mineral oil, collagen, and the like. In the case of formulation, it can be prepared using diluents or excipients such as commonly used fillers, extenders, binders, wetting agents, disintegrants, and surfactants. In particular, sterilized aqueous solutions, non-aqueous solvents, suspensions, emulsions, freeze-dried preparations, suppositories, ointments (for example, dental pulp liner, etc.) may be included. As the non-aqueous solvent and suspension, propylene glycol, polyethylene glycol, vegetable oil such as olive oil, and injectable ester such as ethyl oleate may be used. As a base for suppositories, witepsol, macrogol, tween 61, cacao butter, laurin, glycerogelatin, and the like may be used.

The content of the LPAR2 inhibitor contained in the pharmaceutical composition of the present invention is not particularly limited thereto, but may be included in an amount of 0.0001 to 50% by weight, more preferably 0.01 to 20% by weight, based on the total weight of the final composition.

The pharmaceutical composition of the present invention may be administered in a pharmaceutically effective amount, and the term "pharmaceutically effective amount" of the present invention refers to an amount sufficient to treat or prevent a disease at a reasonable benefit/risk ratio applicable to medical treatment or prevention and the effective dose level can be determined according to factors including disease severity, drug activity, patient's age, weight, health and sex, patient's sensitivity to drugs, administration time, route of administration and rate of excretion vs treatment duration of the composition of the invention used, combination with the composition of the invention used or co-used drugs and other factors well known in the field of medicine. The pharmaceutical composition of the present invention may be administered alone or may be administered in combination with a known pharmaceutical composition for treating dentin-dental pulp disease and/or periodontal disease. Considering all of the above factors, it is important to administer an amount capable of obtaining the maximum effect in a minimum amount without side effects.

The dosage of the pharmaceutical composition of the present invention can be determined by a person skilled in the art in consideration of the purpose of use, the degree of disease addiction, the patient's age, weight, sex, history, or the type of substance used as an active ingredient. For example, the pharmaceutical composition of the present invention may be administered in an amount of about 0.1 ng to about 100 mg/kg, preferably 1 ng to about 10 mg/kg per adult, and the frequency of administration of the composition of the present invention is not particularly limited thereto, but may be administered once a day or several times by dividing the dose. The above dosage does not limit the scope of the present invention in any way.

In another aspect, the present invention provides a method of preventing or treating dentin-dental pulp disease or periodontal disease, comprising administering the pharmaceutical composition in a pharmaceutically effective amount to a subject other than a human having dentin-dental pulp disease or periodontal disease.

The term "subject" of the present invention may include, without limitation, mammals including mice, livestock, etc., which require treatment of dentin-dental pulp disease or periodontal disease, but excludes humans among subjects with the disease.

The route of administration of the pharmaceutical composition of the present invention may be administered through any general route as long as it can reach the target tissue. The pharmaceutical composition of the present invention is not particularly limited thereto, but may be administered through a route such as intraoral administration or intraoral injection, depending on the purpose.

The present invention provides a use of a composition comprising an inhibitor of LPAR2 to prevent or treat dentin-dental pulp disease or periodontal disease.

The present invention provides a composition for promoting regeneration of hard tissues including dentin, bone and cementum or dental pulp tissues comprising LPAR2. As described above, the inhibitor of LPAR2 increases the expression level related to the differentiation of human-derived dental pulp stem cells into bone, dentin and cementoblasts, and also promotes the growth of vascular growth in the early stage and the formation of dentin bridge in the later stages in animal models and it can be used as an active ingredient of a composition for promoting regeneration of hard tissues including dentin, bone and cementum or dental pulp tissues. The composition for promoting regeneration of the present invention may be used as a cell therapy agent for regeneration of hard tissues including dentin, bone and cementum or dental pulp tissues.

As used herein, "cell therapy agent" refers to medicines used for the purpose of treatment, diagnosis and prevention through a series of methods including proliferation or screening of autologous, allogenic, or xenogenic cells in vitro to restore the function of cells and tissues, or changing the biological properties of cells by other methods. Cell therapy products have been managed as pharmaceuticals since 1993 in the US and 2002 in Korea. Such cell therapy agents include, but are not limited to, stem cell therapy agent for tissue regeneration or recovery of specific organ functions.

The present invention provides a method of promoting the regeneration of hard tissues including dentin, bone and cementum or dental pulp tissues, comprising administering a composition for promoting the regeneration of hard tissues including dentin, bone and cementum or dental pulp tissues comprising an inhibitor of LPAR2 to a subject other than humans. The term "subject" of the present invention is as described above.

The present invention provides a use of a composition comprising an inhibitor of LPAR2 to promote the regeneration of hard tissues including dentin, bone and cementum or dental pulp tissues.

The present invention provides a composition for promoting differentiation of odontoblasts, osteoblasts or cementoblasts, comprising an inhibitor of LPAR2. As described above, the inhibitor of LPAR2 promotes the differentiation of bone and odontoblasts, and increases the level of differentiation genes of bone, odontoblasts and cementoblasts to be used as an active ingredient of the composition for promoting differentiation of odontoblasts, osteoblasts or cementoblasts.

The present invention provides a use of a composition comprising an inhibitor of LPAR2 to promote the differentiation of odontoblasts, osteoblasts or cementoblasts.

The present invention provides a quasi-drug composition for preventing or improving dentin-dental pulp disease or periodontal disease comprising an inhibitor of LPAR2.

As used herein, the term "improvement" means any action that at least reduces the severity of a parameter related to the condition being treated, for example, symptoms. The above improvement can be interpreted to mean any action that improves or benefits the symptoms of dentin-dental pulp disease by promoting the regeneration of dentin or dental pulp tissue, or any action that improves or benefits the symptoms of periodontal disease by promoting the regeneration of bones and dentin, by administering a composition comprising an inhibitor of LPAR2 to a subject in need of treatment for dentin-dental pulp disease or periodontal disease.

The term "quasi-drug" of the present invention refers to items that are less effective than pharmaceuticals among items used for diagnosis, treatment, improvement, alleviation, treatment or prevention of diseases of humans or animals. For example, according to the Pharmaceutical Affairs Act, quasi-drugs are those other than those used for pharmaceutical purposes and they includes textiles and rubber products used for the treatment or prevention of diseases of humans and animals, those that have mild or no direct effect on the human body, and non-instruments or non-machines and those similar to instruments or machines, and fungicide or pesticide for preventing infectious diseases.

In the present invention, the type or formulation of the quasi-drug composition comprising an inhibitor of LPAR2 is not particularly limited, but as an example, it may be an oral disinfectant cleaner, an oral cleaning product, toothpaste, dental floss, an oral ointment, and the like.

The present invention provides a health functional food composition for preventing or improving dentin-dental pulp disease or periodontal disease comprising an inhibitor of LPAR2.

As used herein, the term "food" refers to meat, sausage, bread, chocolate, candy, snacks, confectionery, pizza, ramen, other noodles, gum, dairy products including ice cream, various soups, beverages, tea, drinks, alcoholic beverages, vitamin complexes, health functional foods and health foods, and all foods in the usual sense are included.

The health function food is the same term as food for special health use (FoSHU) and refers to foods with high medical and medicinal effects that have been processed to efficiently exhibit body modulating functions, in addition to nutritional supply. As used herein, the term "function(al)" means controlling nutrients on the structure and function of the human body or obtaining useful effects for health purposes such as physiological effects. The food product of the present invention can be prepared by a method commonly used in the art, and during the production, it can be prepared by adding raw materials and ingredients commonly added in the art. In addition, the formulation of the food may be prepared without limitation as long as it is a formulation recognized as a food. The composition for food of the present invention can be prepared in various forms of formulation, and unlike general drugs, it has the advantage of not having side effects that may occur when taking a drug for a long time by using food as a raw material, and is excellent in portability and thus the food of the present invention can be ingested as an adjuvant for enhancing the effect of preventing or improving dentin-dental pulp disease and/or periodontal disease.

The health food refers to a food having positive health maintenance or promotion effect compared to general food, and a health supplement food refers to a food for health supplement purposes. In some cases, the terms of health functional food, health food, and health supplement food may be used interchangeably. Specifically, the health functional food is a food prepared by adding an inhibitor of LPAR2 to food materials such as beverages, teas, spices, gums, confectionery, or encapsulating, powdering, making into suspension, etc. It means that it has a specific effect on health when ingested, but unlike general drugs, it has the advantage that there are no side effects that may occur when taking the drug for a long time by using food as a raw material.

Because it is possible to consume the food composition of the present invention on a daily basis and a high effect can be expected for the prevention or improvement of dentin-dental pulp disease and/or periodontal disease, it can be very useful.

The food composition may further include a physiologically acceptable carrier, and the kind of carrier is not particularly limited, and any carrier commonly used in the art may be used.

In addition, the food composition may include additional ingredients that are commonly used in food compositions to improve smell, taste, and vision. For example, vitamins A, C, D, E, B1, B2, B6, B12, niacin, biotin, folate, panthotenic acid, and the like may be included. In addition, minerals such as zinc (Zn), iron (Fe), calcium (Ca), chromium (Cr), magnesium (Mg), manganese (Mn), and copper (Cu) may be included. In addition, amino acids such as lysine, tryptophan, cysteine, and valine may be included.

In addition, the food composition includes food additives such as preservatives (potassium sorbate, sodium benzoate, salicylic acid, sodium dehydroacetate, etc.), disinfectants (bleaching and highly bleaching, sodium hypochlorite, etc.), antioxidants (butylhydroxyanisole (BHA), butylhydroxytoleuene (BHT), etc.), colorants (tar color, etc.), coloring agents (sodium nitrite, sodium nitrite, etc.), bleach (sodium sulfite), seasoning (MSG sodium glutamate, etc.), sweeteners (dulcin, cyclamate, saccharin, sodium, etc.), flavorings (vanillin, lactones, etc.), expanding agents (alum, D-potassium hydrogen tartrate, etc.), reinforcing agents, emulsifying agents, thickening agents, coating agents, gum base agents, antifoaming agents, solvents, improving agents, etc. The additive can be selected according to the type of food and used in an appropriate amount.

The inhibitor of LPAR2 may be added as it is, or may be used with other foods or food ingredients, and may be appropriately used according to a conventional method. The mixing amount of the active ingredient may be appropriately determined according to the purpose of use (prevention, health or therapeutic treatment). In general, when preparing food or beverage, the food composition of the present invention may be added in an amount of 50 parts by weight or less, specifically 20 parts by weight or less, based on the food or beverage. However, when ingested for a long time for health and hygiene purposes, the content below the above-mentioned range may be included, and since there is no problem in terms of safety, the active ingredient may be used in an amount above the above-mentioned range.

As an example of the food composition of the present invention, it may be used as a health drink composition, and in this case, it may contain various flavoring agents or natural carbohydrates, etc. as an additional ingredient, like a normal beverage. The natural carbohydrates described above include monosaccharides such as glucose and fructose; disaccharides such as maltose and sucrose; polysaccharides such as dextrin and cyclodextrin; sugar alcohol such as xylitol, sorbitol, and erythritol. As sweeteners, natural sweeteners such as thaumatin and stevia extract; synthetic sweeteners such as saccharin and aspartame can be used. The ratio of the natural carbohydrate may be generally about 0.01 to 0.04 g, specifically about 0.02 to 0.03 g per 100 ml of the health beverage composition of the present invention.

In addition to the above, health beverage compositions may include various nutrients, vitamins, electrolytes, flavoring agents, colorants, pectic acid, salts of pectic acid, alginic acid, salts of alginic acid, organic acids, protective colloid thickeners, pH adjusters, stabilizers, preservatives, glycerin, alcohol or a carbonation agent. In addition, it may contain flesh for the manufacture of natural fruit juice, fruit juice beverage, or vegetable beverage. These ingredients may be used independently or in combination. The ratio of these additives is not very important, but it is generally selected from 0.01 to 0.1 parts by weight per 100 parts by weight of the health beverage composition of the present invention.

The food composition of the present invention may be included in various wt % if it can exhibit the effect of preventing or improving dentin-dental pulp disease or periodontal disease, but specifically, the inhibitor of LPAR2 may be included in 0.0001 to 100 wt % or 0.01 to 80 wt % based on the total weight of the food composition, but it is not limited thereto.

Hereinafter, the present invention will be described in more detail through examples. These examples are only intended to illustrate the present invention in more detail, and it will be apparent to those skilled in the art that the scope of the present invention is not limited by these examples according to the gist of the present invention.

Example 1

1-1. Isolation and Culture of Human-Derived Dental Pulp Stem Cells

Human-derived dental pulp stem cells were obtained from dental pulp tissue cells from an anonymous adult male donor's wisdom tooth and were cryopreserved. The dental pulp tissue cells were positive for CD105, CD166, CD29, CD90 and CD73 and negative for CD34, CD45 and CD133. The human-derived dental pulp stem cells were maintained in Miltenyi Stem MACS MSC Expansion Media Kit XF containing 100 μg/ml streptomycin and 100 μg/ml penicillin in a 15 cm culture flask. Human-derived dental pulp stem cells were isolated from culture plates using TrypLE™ Express (Life Technologies) and maintained at a density of 5000-6000 cells/cm$^2$. It is known that human dental pulp stem cells can differentiate into odontoblasts, osteoblasts, cementoblasts and periodontal ligament cells under various conditions (Tissue Eng Part A. 2014 April; 20(7-8):1342-51).

1-2. Reagents and Compounds

AM095, Beck 35, RP10-83 were obtained from Gabor J. Tigiy (UTHSC, Memphis, TN 38163, USA). H2L5186303 was obtained from Tocris Bioscience (Minneapolis, MN). The compound was dissolved in DMSO and used.

1-3. Compound Treatment

LPAR2 antagonists Beck 35 and H2L5186303, LPAR2 agonist RP10-83, and LPAR1 antagonist AM095 were treated every 3 days during proliferation or osteogenic differentiation. Concentration range of Beck 35 treatment was 0.5 μM to 10 μM, H2L5186303 was 10 μM to 100 μM, and RP10-83 and AM095 were 1 μM to 10 μM.

Example 2

2-1. Cell Viability Measurement

Cell viability measurement was evaluated by the 3-(4,5-dimethylthiazol-2-yl)-2,5-diphenyl-2H-tetrazolium bromide (MTT) method. Human-derived dental pulp stem cells were coated with 0.2% gelatin one day before culture. On the day of incubation, 0.2% gelatin was removed from the 48-well plate and washed once with PBS. In 48-well plates, human-derived dental pulp stem cells (4×10$^5$ cells/ml) were cultured in Miltenyi Stem MACS MSC Expansion Media Kit XF medium containing 100 μg/ml streptomycin and 100 μg/ml penicillin. Beck 35 was evaluated at various concentrations (0, 0.1, 1 and 1.0 μg/ml) for 24 hours at 37° C. in an atmosphere of 5% CO$_2$ and 95% humidity. Then, the cells were incubated with 0.5 mg/ml MTT (SIGMA, USA) for 3 hours, and the reaction was stopped by adding dimethyl sulfoxide (DMSO, JUNSEL, Japan). Results were obtained at 560 nm using an ELISA reader. The cell viability of the control cells was used as a 100% control value.

As a result, as shown in FIG. 1A, it was confirmed that the Beck 35 of 0.1 and 1 μM/ml was not different from the control, but the Beck 35 of 10 μM/ml promoted the proliferation of human-derived dental pulp stem cells.

In addition, human-derived dental pulp stem cells were cultured in bone differentiation inducing medium (10% fetal bovine serum, 0.1 mM dexamethasone, 10 mM β-glycerophosphate and 50 mM ascorbic acid) for 24 hours to induce the differentiation and various concentrations (1, 5 and 1.0 µM/ml) of Beck 35 were treated during differentiation. As a result, as shown in FIG. 1B, while human-derived dental pulp stem cells were differentiated, Beck 35 at concentrations of 1, 5 and 1.0 µM/ml inhibited the proliferation of human dental pulp stem cells.

2-2. Measurement of Extracellular Matrix Calcification of Effect of Beck, an Inhibitor of LPAR2, on Bone Differentiation in Human-Derived Dental Pulp Stem Cells by Alizarin Red S Staining Human-derived dental pulp stem cells (4×10$^5$ cells/ml) were cultured in Miltenyi Stem MACS MSC Expansion Media Kit XF medium containing 100 µg/ml streptomycin and 100 µg/ml penicillin, followed by culturing in bone differentiation induction medium (10% fetal bovine serum, 0.1 mM dexamethasone, 10 mM β-glycerophosphate, and 50 mM ascorbic acid). Beck 35 (LPAR2 inhibitor) and LPA were added to the bone differentiation induction medium at various concentrations (0, 1, 5 and 1.0 µM/ml). The cells in which bone differentiation was induced were washed twice with PBS, fixed with 70% ethanol at 4° C. for 1 hour, stained with 40 mM Alizarin Red S (pH 4.2, Sigma Co.) solution for 10 minutes, and then washed with distilled water sufficiently and the degree of calcium nodule formation was observed with an optical microscope. In order to quantify the degree of staining, the absorbance was measured at 562 nm after dissolving in 10% (WN) cetylpyridinium chloride and 10 mM sodium phosphate (pH 7.0) solution.

As a result, as shown in FIG. 2, the LPA-treated group did not undergo the calcification, while the LPAR2 inhibitor Beck 35-treated group promoted the calcification in a concentration-dependent manner.

2-3. Electron Microscope Analysis

As in Example 2-2, human-derived dental pulp stem cells were cultured in a culture medium for inducing bone differentiation with or without Beck 35, an inhibitor of LPAR2, to induce bone differentiation, and then observed by an electron microscope.

As a result, as shown in FIG. 3A and FIG. 3B, relatively long-shaped cells in the group treated with Beck 35 were observed, and a shape in which the head and tail of the cells were clearly distinguished was observed. On the other hand, in the group not treated with Beck 35, a generally round shape was observed and no specially differentiated findings were observed. A picture of this in more detail is shown in FIG. 3C. As a result of confirming the shape by joining several photographs on an enlarged scale, a large nucleus was observed in the head and numerous organelles were observed in the trunk.

In order to more clearly compare this, the results of comparative analysis with the dental blast cells extracted from Google's Wikimedia in FIG. 3C were found to be morphologically very similar to the group treated with Beck 35. In addition, as a result of confirming the distribution of organelles in the cell by enlarging FIG. 3C, a large nucleus was observed in the front of the differentiated dental blast cells, and the activity of lysosomes in front of the nucleus appears to be high, which is shown to be highly responsible for intracellular clearance. The various organelles seen in the body are in the form of cytoplasmic reticulum and Golgi, and in particular, as the number of mitochondria involved in energy metabolism is observed to be remarkably large, it is shown that the activity of synthesizing an energy source ATP is high. As a result of observing the outer wall of the cell, a lot of vesicle structures in the form of balloons distributed in the outer membrane were observed, and it was shown to be for metabolism, transportation, storage of enzymes, and chemical reaction sites.

2-4. Real-Time PCR Analysis

As in Example 2-2, human-derived dental pulp stem cells were differentiated for 7 days, 14 days and 21 days in a bone differentiation induction culture medium. Beck 35 was added to the bone differentiation medium at a concentration of 1 µM once every 3 days to differentiate for a week. Those maintained with the human-derived dental pulp stem cells, induced differentiation for 7 days, 14 days and 21 days with bone differentiation medium, and induced differentiation for 7 days in bone differentiation medium containing Beck 35 was used to isolate total RNA with Trisure (Bioline, UK) and reverse transcription to cDNA was performed using HelixCript™ Thermo Reverse Transcriptase (NanoHelix, Korea, Daejeon, Korea). The synthesized cDNA was performed using the primers of Table 1 and Power SYBR Green PCR Master Mix. The data analysis was determined using the delta Ct method.

TABLE 1

|  | Forward | Reverse |
| --- | --- | --- |
| GAPDH | GAA GGT GAA GGT CGG AGT (SEQ ID NO: 2) | GAA GAT GGT GAT GGG ATT TC (SEQ ID NO: 3) |
| OPN | CTC CAT TGA CTC GAA CGA CTC (SEQ ID NO: 4) | CAG GTC TGC GAA ACT TCT TAG AT (SEQ ID NO: 5) |
| RUNX2 | TCT TAG AAC AAA TTC TGC CCT TT (SEQ ID NO: 6) | TGC TTT GGT CTT GAA ATC ACA (SEQ ID NO: 7) |
| DMP-1 | CAA GAC AGT GCC AAG AT AC (SEQ ID NO: 8) | TTC CCT CAT CGT CCA ACT (SEQ ID NO: 9) |
| DSPP | CTG GTG CAT GAA GGT GAT AG (SEQ ID NO: 10) | CCC TCT TCG TTT GCT AAT GT (SEQ ID NO: 11) |

As a result, as shown in FIG. 4, the expression levels of genes related to the differentiation of bone, odontoblasts and cementoblasts of DSPP (dentin sialophosphoprotein), DMP-1 (dentin matrix protein 1), Runx2 (runt-related transcription factor 2), and osteopontin were Increased.

2-5. Measurement of Extracellular Matrix Calcification of Effect of LPAR2 Agonists and Antagonists on Bone Differentiation in Human-Derived Dental Pulp Stem Cells by Alizarin Red S Staining Human-derived dental pulp stem cells ($4\times10^5$ cells/ml) were cultured in Miltenyi Stem MACS MSC Expansion Media Kit XF medium containing 100 µg/ml streptomycin and 100 µg/ml penicillin, and differentiation was induced for 14 days by changing to the bone differentiation induction medium. To the bone differentiation induction medium, RP10-83, an agonist of LPAR2 and H2L5186303, an antagonist of LPAR2 were added at various concentrations (0, 1, and 10 µM/ml). The cells in which bone differentiation was induced were washed twice with PBS, fixed with 70% ethanol at 4° C. for 1 hour, stained with 40 mM Alizarin Red S (pH 4.2, Sigma Co.) solution for 10 minutes, and then washed with distilled water sufficiently. In order to quantify the degree of staining, the absorbance was measured at 562 nm after dissolving in a 10% (WN) cetylpyridinium chloride and 10 mM sodium phosphate (pH 7.0) solution.

As a result, as shown in FIG. 5, the group treated with H2L5186303, an antagonist of LPAR2, promoted bone differentiation as in Beck 35, but RP10-83, an agonist of LPAR2, inhibited bone differentiation.

2-6. Measurement of Extracellular Matrix Calcification of Effect of Si-RNA, Another Inhibitor of LPAR2, on Bone Differentiation in Human-Derived Dental Pulp Stem Cells by Alizarin Red S Staining Human-derived dental pulp stem cells ($4\times10^5$ cells/ml) were cultured in a growth medium without antibiotics. 50 nM of LPAR2 si-RNA was transfected using jetPRIME (Polyplus Transfection) according to the manufacturers protocol. As a control, non-targeting siRNA (SEQ ID NO: 1: GGCCAACUCACUGGUCAAUT-TAUUGACCAGUGAGUUGGCCTT) was transfected. The differentiation of the cells was induced for 7 days after changing to bone differentiation induction medium. The cells in which bone differentiation was induced were washed twice with PBS, fixed with 70% ethanol at 4° C. for 1 hour, stained with 40 mM Alizarin Red S (pH 4.2, Sigma Co.) solution for 10 minutes, and then washed with distilled water sufficiently.

As a result, as shown in FIG. 6A, the si-LPAR2-transfected group had the same change of cell morphology as the Beck 35-treated group. Each LPAR expression was inhibited with si-LPAR1-3 to confirm that the cell morphology was changed by Beck 35 was specific for LPAR2. In order to verify the specificity of si-LPAR2, si-LPAR1-3 was treated with dental pulp stem cells, respectively, and the expression of LPAR1-3 was confirmed by real-time PCR (FIG. 6B and FIG. 6C). Dental pulp stem cells with reduced expression of LPAR1-3 were induced to differentiate in bone differentiation medium (FIG. 6D and FIG. 6E). It was confirmed that ARS was specifically increased in si-LPAR2. Therefore, it can be seen that inhibition of LPAR2 specifically promotes the differentiation of dental pulp stem cells.

2-7. Real-Time PCR Analysis During Differentiation of Bone and Odontoblasts from Human-Derived Dental Pulp Stem Cells As in Example 2-2, human-derived dental pulp stem cells were differentiated for 7 days, 14 days and 21 days in a bone differentiation induction culture medium. Beck 35 was differentiated for a week by adding in the bone differentiation medium once every 3 days at a concentration of 1 µM. Those maintained with the human-derived dental pulp stem cells, induced differentiation for 7 days, 14 days and 21 days with bone differentiation medium, and induced differentiation for 7 days in bone differentiation medium containing Beck 35 was used to isolate total RNA with Trisure (Bioline, UK) and reverse transcription to cDNA was performed using Helix-Cript™ Thermo Reverse Transcriptase (NanoHelix, Korea, Daejeon, Korea). The synthesized cDNA was performed using the primers of Table 2 and Power SYBR Green PCR Master Mix. The data analysis was determined using the delta Ct method.

TABLE 2

|  | Forward | Reverse |
|---|---|---|
| GAPDH | GAA GGT GAA GGT CGG AGT (SEQ ID NO: 2) | GAA GAT GGT GAT GGG ATT TC (SEQ ID NO: 3) |
| LPAR2 | GTC CTC ATT ACC CAG TCA TAC CG (SEQ ID NO: 12) | CTG ATG GAC TCC ACC CTT TAG CT TAG CT (SEQ ID NO: 13) |

As a result, it was confirmed that the expression level of LPAR2 was decreased as shown in FIG. 7.

Example 3

3-1. Animal Model

Experimental animals were carried out using mouse ICR-based male 8 week-old mice. After anesthesia is performed by administering intraperitoneally Zoletil (Virbac, Carros, France) and Rompun (Bayer, Berlin, Germany), which are anesthetic inducing agents according to the weight, an experiment was conducted to expose the pulp cavity for the maxillary right first molars. To confirm the change in gene expression, an experiment was conducted on the developing 14th day pregnant embryo. ICR-based female mice whose pregnancy was confirmed were sacrificed in the morning of the 14th day after pregnancy, and then embryos were obtained and the tooth germ of the lower jaw was finely dissected under a stereoscopic microscope, and the tooth germ tissue was placed on the lid of a 35 mm diameter Petri dish for experimentation together with the culture solution and cultured in a 5% carbon dioxide incubator at 37° C. for 24 hours with or without Beck 35 drug administration.

3-2. Hematoxylin and Eosin Stain (H&E)

In order to prepare tissue sections, mice were sacrificed after a certain experimental period in the experimental group and the control group, fixed in 4% paraformaldehyde, washed with phosphate buffer solution, and demineralized in 0.1 M EDTA chelate solution. Demineralization proceeded for 4 weeks, and after demineralization, it was embedded in wax, cut to a thickness of 7 micrometers, and smeared on a glass slide to perform conventional hematoxylin and eosin staining.

As a result of treatment with Beck 35 in the animal model, after 3 and 5 days of the Beck 35 treatment group, the cell nuclei in the pulp cavity were stained lighter than the control group, and more tissues were observed as blood vessels. Also, in the control group, the number of inflammatory cells was observed higher than that of the treatment group. After 42 days, in the treatment group, the formation of dentin bridge was clearly observed, but in the control group, it was confirmed that the formation of dentin was incomplete.

3-3. Masson Trichrome Staining (MTC)

MTC staining was performed to confirm the synthesis of collagen protein and formation of mineralized tissue. After staining the nucleus with hematoxylin for the tissue on the glass slide produced through the normal tissue sectioning process and if the entire tissue is stained with a mixed dyeing solution designed to perform cytoplasmic staining with biebrich scarlet and muscle fibers staining with acid fuchsin, all of collagen fibers, muscle fibers and cytoplasm can be observed by staining red.

As a result of confirming through MTC staining, it was confirmed that the same blood vessel distribution as the HE staining result was found in the treatment group 3 and 5 days later, and the number of cells in which the inflammatory cells and the nucleus were thickly condensed was small. After 42 days, the formation of calcified dentin bridge was confirmed in the treatment group compared to the control group.

3-4. Micro-CT Examination

Microcomputerized tomography was performed to confirm the hard tissue regenerated by the drug. The lower jaw tissue fixed in 4% paraformaldehyde was observed using Skyscan1272 (Bruker, Kontich, Belgium), and 2 micrometers pixels were photographed at 4904×3280 resolution for the entire 360 degree, and the image was reconstructed in 3D with a data viewer and then the degree of hard tissue formation was objectively analyzed by analyzing with the CTAn (Bruker) program.

After 42 days from the pulp cavity exposure experiment, it was confirmed that dentin bridge was formed in the treatment group, but in the control group, it was confirmed that the formation of dentin bridge was incomplete.

3-5. Pulp Cavity

While observing the oral cavity of anesthetized mice under a stereoscopic microscope, a pulp cavity exposure experiment was performed on the upper right first molar, and the left upper first molar was used as a untreated control. While observing with a stereoscopic microscope, using a round burr having 0.6 mm diameter connected to a high-speed handpiece, the enamel and dentin was exposed to be perpendicular to the occlusal surface, and when necessary, water was sprayed to minimize tissue damage. Afterwards, the Beck 35 drug was mounted on Pluronic F127 and delivered to the exposed pulp cavity. Only Pluronic F127 was delivered to confirm as a control. After the delivery of the Beck 35 drug to the pulp cavity, the doubly exposed pulp cavity was covered with Dycal (Dentsply Caulk, Milford, DE) and a stereoscopic composite resin. Thereafter, on the 3rd, 5th and 42nd days, the changes were confirmed by histological and microcomputed tomography techniques.

As a result of micro-CT examination, it was confirmed that the perfect dentin bridge was regenerated (FIG. 8).

3-6. Immunohistochemistry Method

To confirm the expression of the protein, the expression pattern of NESTIN, a protein specific for odontoblasts, was confirmed by immunohistochemistry using tissue sections from the control and treatment groups. The expression of the protein was confirmed based on the antigen-antibody reaction, and the positive reaction of the protein was confirmed as brown with 3,3'-diaminobenzidine.

In the case of NESTIN and RUNX2, after 3 and 5 days passed in the treatment group, more positive reactions were confirmed in the pulp cavity periphery than the control group (FIG. 8).

3-7. Real-Time PCR Analysis

In order to confirm the change in gene expression by Beck 35 drugs, in vitro culture was performed by microdissecting the tooth germ at the 14th day of the embryonic period, and the group treated with the drug for 24 hours was set as the experimental group, and the untreated tissue was set as the control group, and changes in gene expression were confirmed by real-time PCR analysis. After RNA was obtained from the cultured tissue, the first strand cDNA was synthesized and the expression level was confirmed by real-time PCR for genes known to be important for dentin formation until now.

First, as a result of isolating and culturing tooth germ mesenchyme, it was confirmed that in the experimental group treated with Beck 35 for 24 hours, the expression of genes involved in Wnt signaling, Axin2, beta-Catenin, and Lef1, were reduced compared to the control group and the expression of genes Bmp2, Bmp4, Bmp6, and Bmp7, which are genes involved in Bmp signaling, were reduced (FIG. 9A).

On the other hand, when the dental papilla mesenchyme, which developed into dental pulp, was isolated and cultured, in the experimental group treated with Beck 35 for 24 hours, overall gene expression increased compared to the control group, and in particular, the expression of Bmp6 was confirmed to be increased (FIG. 9B). As such, it was confirmed that Beck 35, an inhibitor of LPAR2, increases gene expression which is important for dental pulp development and development process.

While the present invention has been particularly described with reference to specific embodiments thereof, it is apparent that this specific description is only a preferred embodiment and that the scope of the present invention is not limited thereby to those skilled in the art. That is, the practical scope of the present invention is defined by the appended claims and their equivalents.

The invention claimed is:

1. A method of treating dentin-dental pulp disease comprising:

administering a pharmaceutical composition comprising a LPAR2 (lysophosphatidic acid receptor 2) inhibitor, which is the following Chemical Formula 1 to a subject, <Chemical Formula 1>

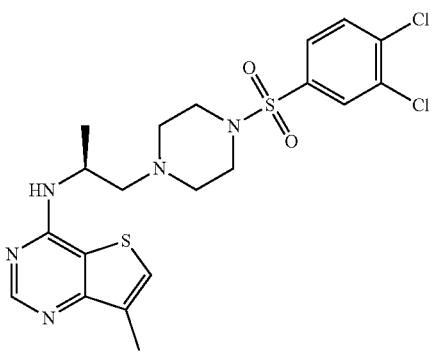

wherein the pharmaceutical composition promotes regeneration of hard tissues including dentin, bone and cementum or dental pulp tissues.

2. The method of claim 1, wherein the dentin-dental pulp disease is dentin hypersensitivity, hyperemia of pulp, pulpitis, pulp degeneration, pulp necrosis or gangrene.

3. A method of promoting differentiation from human-derived dental pulp stem cells into odontoblasts, osteoblasts or cementoblasts, comprising:

administering a composition comprising a LPAR2 (lysophosphatidic acid receptor 2) inhibitor, which is the following Chemical Formula 1 to a subject, <Chemical Formula 1>

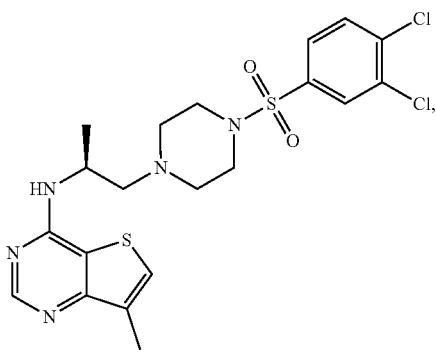

wherein the differentiation from human-derived dental pulp stem cells into odontoblasts, osteoblasts or cementoblasts is promoted.

4. A method of improving dentin-dental pulp disease comprising:

administering a quasi-drug composition comprising a LPAR2 (lysophosphatidic acid receptor 2) inhibitor, which is the following Chemical Formula 1 to a subject, <Chemical Formula 1>

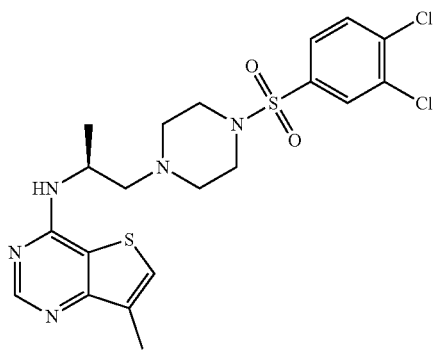

wherein the quasi-drug composition promotes regeneration of hard tissues including dentin, bone and cementum or dental pulp tissues.

* * * * *